United States Patent [19]

Link

[11] Patent Number: 4,634,442
[45] Date of Patent: Jan. 6, 1987

[54] INTRAOCULAR LENS WITH A VAULTED OPTIC

[75] Inventor: William J. Link, Irvine, Calif.

[73] Assignee: American Hospital Supply Corporation, Deerfield, Ill.

[21] Appl. No.: 656,074

[22] Filed: Sep. 28, 1984

[51] Int. Cl.⁴ .............................................. A61F 4/16
[52] U.S. Cl. ....................................................... 623/6
[58] Field of Search ............................................ 623/6

[56] References Cited

U.S. PATENT DOCUMENTS

| 4,146,138 | 3/1979 | Davis | 248/231.8 X |
| 4,159,546 | 7/1979 | Shearing . | |
| 4,244,060 | 1/1981 | Hoffer . | |
| 4,412,359 | 11/1983 | Myers | 623/6 |
| 4,547,914 | 10/1985 | Castleman | 623/6 |
| 4,562,600 | 1/1986 | Ginsberg | 623/6 |

FOREIGN PATENT DOCUMENTS

| 8336372 | 12/1983 | Fed. Rep. of Germany | 623/6 |
| 0128784 | 3/1984 | France | 623/6 |
| WO84/00883 | 3/1984 | PCT Int'l Appl. | 623/6 |

OTHER PUBLICATIONS

American Medical Optics "PC-15L Posterior Chamber Intraocular Lens" Style Sheet, Oct. 1983.
"The 'Soft J' Loop Posterior Chamber Lens", CILCO advertisement, 3/81.
"The Kratz 'Soft J' Loop Posterior Chamber Lens From CILCO", CILCO, date unknown.
"New The Model 150 Pearce Vaulted Y Posterior Chamber Lens", COBURN advertisement, dated unknown.
"Current Concepts in Cataract Surgery", Selected Proceedings of the Sixth Biennial Cataract Surgical Congress, C. William Simcoe, Library of Congress, Houston, Tex. 1978, pp. 133-143.
"Ovoid Optic Posterior Chamber Intraocular Lens: The First One Hundred Cases", American Intra-Ocular Implant Society Journal, Henry M. Clayman, M.D., vol. 8, No. 4, pp. 343-345, Fall 1982.

Primary Examiner—Richard J. Apley
Assistant Examiner—James Prizant
Attorney, Agent, or Firm—Gordon L. Peterson

[57] ABSTRACT

An intraocular lens, including an optic having an optic body with a posterior surface and first and second circumferentially spaced spacing tabs at the periphery of the optic body. Each of the spacing tabs extends radially outwardly from the periphery of the optic body and axially of the optic body in the same axial direction. A haptic is mounted on the optic and projects generally radially outwardly of the periphery of the optic. With this construction, the intraocular lens can be implanted in the eye, with the spacing tabs in contact with the wall of the capsular bag to space the posterior surface of the optic from the wall of the capsular bag.

11 Claims, 7 Drawing Figures

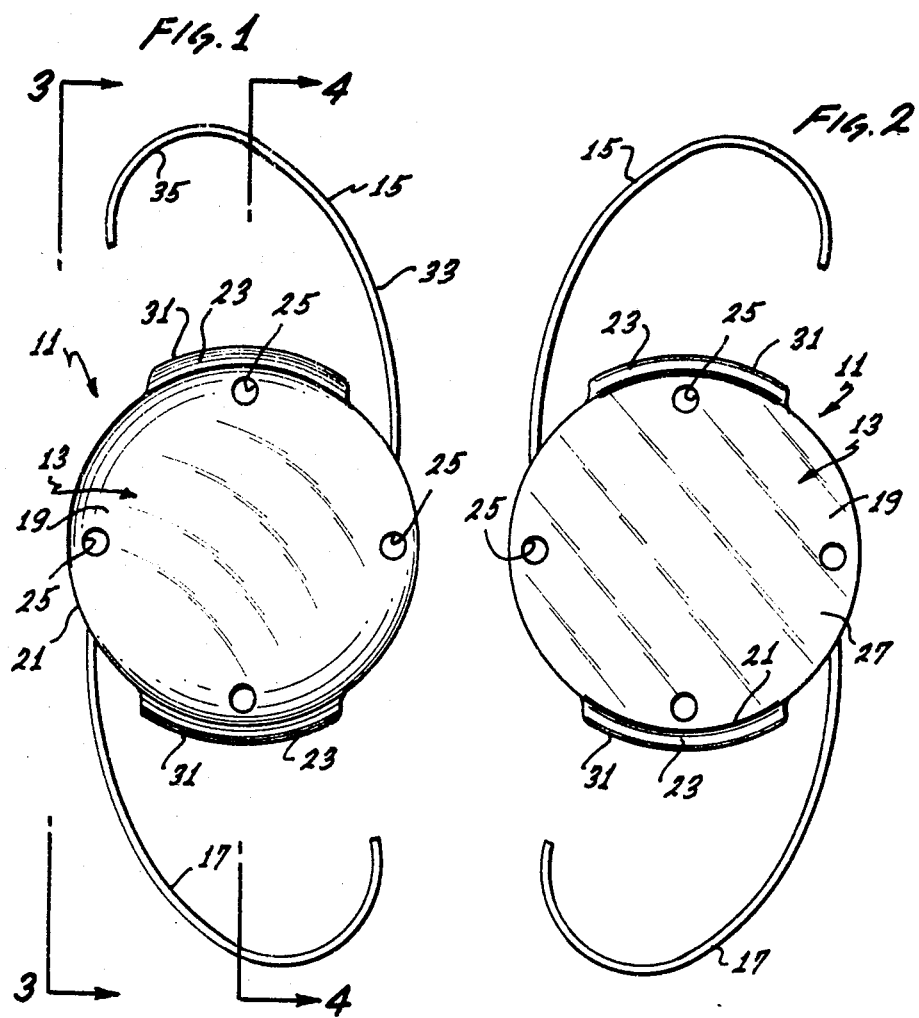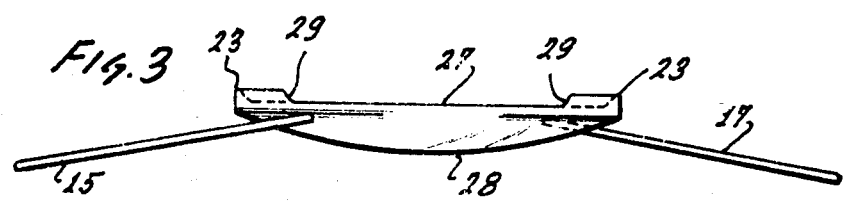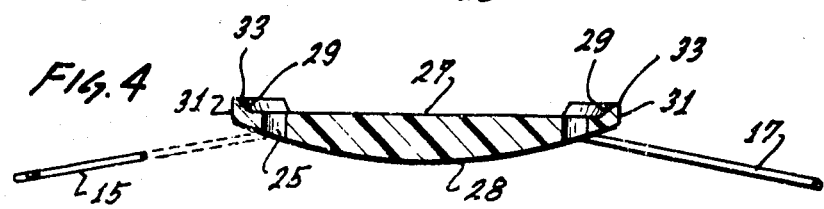

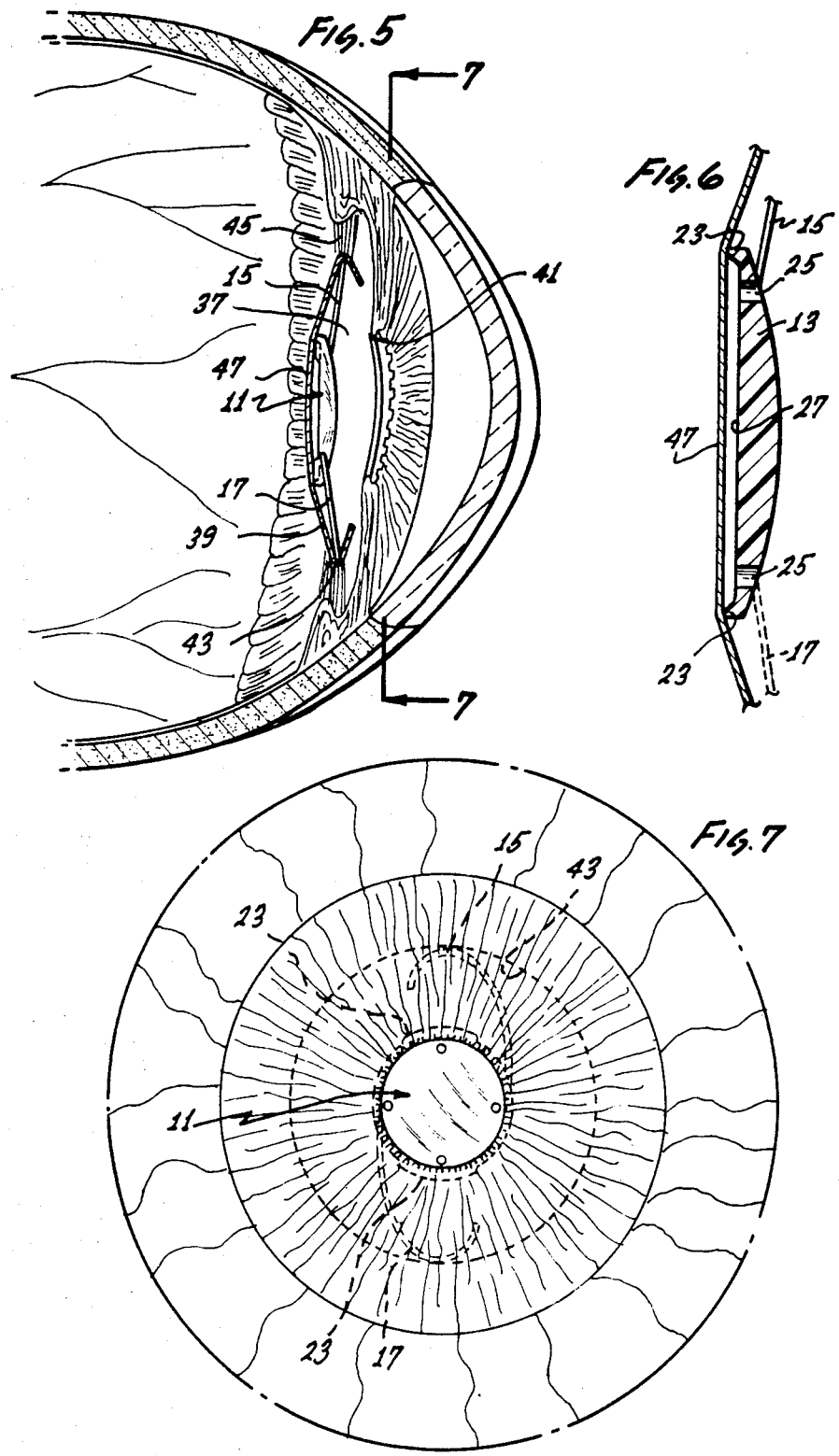

INTRAOCULAR LENS WITH A VAULTED OPTIC

BACKGROUND OF THE INVENTION

In cataract surgery, the natural lens is removed. To refocus the light on the retina and thus restore vision, an intraocular lens is implanted in place of the natural lens.

The intraocular lens can be implanted at various locations within the eye, such as within the capsular bag in the posterior chamber. After implantation of the intraocular lens in the capsular bag, it is sometimes necessary to perform a surgical technique known as discission in which an opening is formed in the posterior capsule. Discission has been performed with mechanical cutting instruments, such as a needle, and more recently, with a surgical laser. Discission may be necessary, for example, to restore vision that has become clouded following implantation of the intraocular lens.

A typical intraocular lens includes an optic and a haptic, with the optic having a flat posterior surface which seats against the posterior capsule. To avoid pitting of the posterior surface of the optic when discission is carried out with a surgical laser, it is necessary to space the posterior surface from the posterior capsule.

One way of spacing the posterior surface of the optic from the posterior capsule is to form an annulus on the posterior surface of the optic, and examples of such construction are shown in Shearing U.S. Pat. No. 4,159,546 and Hoffer U.S. Pat. No. 4,244,060. Alternatively, the posterior surface of the optic can be made concave so that the posterior periphery of the optic engages the posterior capsule with central regions of the posterior surface being spaced from the posterior capsule. Unfortunately, these annular posterior projections on the optic tend to hamper insertion of the intraocular lens into the eye. They also enable wrinkles to form in the posterior capsule and impair the removal of wrinkles in the posterior capsule. Wrinkles are undesirable when discission is being carried out.

SUMMARY OF THE INVENTION

This invention provides an intraocular lens which spaces the posterior surface of the optic from the posterior capsule and which is easier to insert into the eye. This is accomplished by eliminating the annular projections of the prior art in favor of at least two spacing tabs which extend radially outwardly from the periphery of an optic body and axially of the optic body in the same axial direction. The tabs provide a convenient "lead in" for the intraocular lens through the incision in the eye and help the intraocular lens slide across the iris. This is somewhat unexpected in that it would be expected that the tab would tend to hang up on the incision rather than act to conveniently lead the optic into the incision. Of course, the annular projections of the prior art have no lead in capability.

The tabs are also useful in removing wrinkles which may form in the posterior capsule. In this regard, the tabs engage the posterior capsule so that, when the optic is biased posteriorly by the haptic, the tabs bear against the posterior capsule and tend to stretch the posterior capsule so as to eliminate wrinkles. Because the tabs are spaced circumferentially, there is no material between them to inhibit stretching of the posterior capsule.

Each of the spacing tabs has an inner circumferentially extending surface which is inclined radially outwardly at a first angle as it extends axially. One advantage of this inclined surface is that it provides for more secure gripping of the intraocular lens with a forceps. Accordingly, this further facilitates insertion of the intraocular lens into the eye.

To at least assist in retaining the intraocular lens in the implanted condition, the intraocular lens includes a haptic mounted on the optic and projecting generally radially of the optic. In a preferred construction, the haptic includes first and second resilient strands extending from the periphery of the optic body at locations spaced circumferentially from the spacing tabs. Each of the strands extends radially outwardly of the periphery of the optic body a greater radial distance than the spacing tabs. Each of the strands has a region of contact with the eye in the implanted condition, and central portions of such regions are generally radially aligned with the central portions of the spacing tabs, respectively, when the intraocular lens is implanted in the eye.

Preferably, there are two of the tabs arranged generally opposite to each other, although three or more tabs could be provided, if desired. The tabs are preferably imperforate and the optic body has positioning apertures adjacent its periphery. The tabs can extend circumferentially varying amounts, but preferably, each of the tabs does not extend for more than 75 degrees.

The invention, together with additional features and advantages thereof, may best be understood by reference to the following description taken in connection with the accompanying illustrative drawing.

BRIEF DESCRIPTION OF THE DRAWING

FIG. 1 is a front elevational view of an intraocular lens constructed in accordance with the teachings of this invention.

FIG. 2 is a rear elevational view of the intraocular lens.

FIGS. 3 and 4 are views taken generally along lines 3—3 and 4—4, respectively, of FIG. 1.

FIG. 5 is a sectional view through the human eye, with the intraocular lens implanted.

FIG. 6 is an enlarged fragmentary sectional view illustrating the spacing between the posterior surface of the optic body and the posterior capsule.

FIG. 7 is a sectional view taken generally along line 7—7 of FIG. 5.

DESCRIPTION OF THE PREFERRED EMBODIMENT

FIGS. 1 and 2 show an intraocular lens 11 which includes an optic 13 and a haptic in the form of resilient strands 15 and 17. The optic 13 comprises an optic body 19 having a circular periphery 21 and identical spacing tabs 23 extending radially outwardly from the periphery 21. The tabs 23 also extend axially of the optic body in the posterior direction.

The intraocular lens 11 is adapted to replace the natural lens of the human eye, and the optic body 19 may be, for example, a plano-convex lens of suitable diopter power. The optic 13 may be constructed of a suitable biocompatible material, such as polymethylmethacrylate.

The optic 13 has positioning apertures 25 (four being illustrated) closely adjacent the periphery 21. The optic body 19 has a flat, posterior surface 27 and a convex surface 28.

The spacing tabs 23 are spaced circumferentially and diametrically opposed. The tabs 23 need not be diametrically opposite, but preferably, central regions of the tabs are not offset more than 35 to 38 degrees from being diametrically opposite. Each of the spacing tabs 23 extends circumferentially for no more than about 75 degrees, and a circumferential extent of 60 to 65 degrees is preferred. Each of the spacing tabs 23 extends radially of the periphery 21 for only a short distance, such as about 0.25 mm. Each of the spacing tabs 23 is imperforate.

As shown in FIGS. 3 and 4, each of the spacing tabs 23 has an inner circumferentially extending surface 29 which is inclined radially outwardly as it extends axially from the posterior surface 27 toward the posterior of the intraocular lens. Preferably, the surface 29 forms a 45-degree angle with an extension of the posterior surface 27 or a 135-degree angle with the radial inward regions of the posterior surface 27. The circumferential surface 29 extends circumferentially for the full circumferential length of the associated spacing tab 23.

Each of the spacing tabs 23 also has a peripheral surface 31 which forms a segment of an axially short cylinder. The surfaces 29 and 31 are blended together by a curved surface 33 as shown in FIG. 4.

The strands 15 are integrally constructed of a flexible resilient material, such as polypropylene. The particular construction of the strands 15 and 17 is not important to this invention, however, preferably, each of the strands is suitably attached to, and projects from, the optic 13 at locations circumferentially intermediate the spacing tabs 23. The strands 15 and 17 project generally radially outwardly of the optic 13 and may be of various different configurations.

In the illustrated embodiment, the strands 15 and 17 extend anteriorly as they extend radially outwardly (FIGS. 3 and 4). As viewed in FIGS. 1 and 2, the strands 15 and 17 have a curved proximal section 33 which extends generally radially outwardly of the optic 13 and a more sharply curved distal section 35 which curves generally back toward the optic 13. As viewed in FIGS. 1 and 2, the strands 15 and 17 appear to partially encircle the associated tabs 23, and they extend substantially radially beyond the tabs.

FIGS. 5–7 show the intraocular lens 11 implanted in the posterior chamber 37 in the capsular bag 39 behind the iris 41. Although the intraocular lens 11 can be affixed in different ways within the capsular bag 39, as shown in FIG. 5, the strands 15 and 17 engage a generally circular equatorial zone 43 of the capsular bag 39 to retain the intraocular lens 11 in position. When so mounted, the strands 15 and 17 are resiliently deformed to retain the optic 13 essentially coaxial with the iris 41. When deformed in this manner, the strands 15 and 17 have a region of contact with the equatorial zone 43, and central portions of such regions are generally radially aligned with central portions of the spacing tabs 23 as shown in FIG. 7. In the form of mounting shown in FIGS. 5–7, the ciliary body 45 is not contacted by the strands 15 and 17.

As best shown in FIG. 6, the strands 15 and 17 resiliently urge the optic 13 posteriorly and the spacing tabs 23 into contact with the posterior capsule 47 or posterior wall of the capsular bag 39 to space the posterior surface 27 anteriorly of the posterior capsule. Accordingly, discission can be carried out with a surgical laser without pitting the optic 13. In addition, the spacing tabs 23 are resiliently urged against the posterior capsule 47, and this tends to stretch the posterior capsule to remove wrinkles and to resist formation of new wrinkles. This wrinkle-inhibiting feature is particularly effective against wrinkles which extend generally transverse to a line between central regions of the spacing tabs 23.

The intraocular lens 11 can be implanted in accordance with known techniques. However, the tabs 23 can be used to form a lead in into and through the incision in the eye and across the iris 41. In addition, the surface 29 of the tab 23 forms a region which can be conveniently and securely gripped with forceps or other suitable instruments. If the surface 29 were a flat radial surface, only the radial inner edge of such surface would contact the forceps when the intraocular lens 11 was gripped with forceps. However, because the surface 29 is inclined, it provides a surface area, rather than only a line, to engage the forceps when the lens 11 tilts.

Although an exemplary embodiment of the invention has been shown and described, many changes, modifications and substitutions may be made by one having ordinary skill in the art without necessarily departing from the spirit and scope of this invention.

I claim:

1. An intraocular lens with a vaulted optic for implantation in the posterior chamber of the eye with the optic being in the capsular bag, said intraocular lens comprising:

an optic having an optic body with a posterior surface and first and second circumferentially spaced spacing tabs at the periphery of the optic body;

each of said first and second spacing tabs extending radially outwardly from the periphery of the optic body and axially of the optic body in a first axial direction; and a haptic mounted on the optic and projecting generally radially outwardly of the periphery of the optic whereby the intraocular lens can be implanted in the eye with the haptic at least assisting in retaining the optic in the posterior chamber with the spacing tabs in contact with the posterior capsule of the capsular bag to space the posterior surface of the optic from the posterior capsule.

2. An intraocular lens as defined in claim 1 wherein said first spacing tab has an inner circumferentially extending surface which is inclined radially outwardly at a first angle as it extends axially in said first axial direction.

3. An intraocular lens as defined in claim 1 wherein said first angle is about 45 degrees.

4. An intraocular lens as defined in claim 1 wherein said haptic includes first and second resilient strands extending from the periphery of the optic body at locations spaced circumferentially from the spacing tabs, each of said strands extends radially outwardly of the periphery of the optic body for a greater radial distance than said spacing tabs.

5. An intraocular lens as defined in claim 4 wherein each of said strands has a region of contact with the eye in the implanted condition, central portions of said regions being generally radially aligned with the central portions of said spacing tabs, respectively.

6. An intraocular lens as defined in claim 1 wherein there are only two of said spacing tabs and neither of said spacing tabs extends circumferentially for more than about 75 degrees, said spacing tabs being generally opposite each other.

7. An intraocular lens as defined in claim 6 wherein said spacing tabs are imperforate and said optic body has positioning apertures adjacent the periphery of the optic body.

8. An intraocular lens as defined in claim 7 wherein said first spacing tab has an inner circumferentially extending surface which is inclined radially outwardly at a first angle as it extends axially in said first axial direction, said haptic includes first and second resilient strands extending from the periphery of the optic body at locations spaced circumferentially from the spacing tabs, each of said strands extends radially outwardly of the periphery of the optic body for a greater radial distance than said spacing tabs and each of said strands has a region of contact with the eye in the implanted condition, central portions of said region being generally radially aligned with the central portions of said spacing tabs, respectively.

9. An intraocular lens as defined in claim 1 wherein said first tab is imperforate.

10. An intraocular lens as defined in claim 1 wherein said haptic extends radially outwardly of said optic body a greater radial distance than either of said tabs.

11. An intraocular lens as defined in claim 1 wherein each of said tabs extends radially outwardly of the periphery of the optic body no more than about 0.25 millimeter.

* * * * *